US008772040B2

(12) United States Patent
Shin et al.

(10) Patent No.: US 8,772,040 B2
(45) Date of Patent: Jul. 8, 2014

(54) APPARATUS AND METHOD OF PLATELET MULTI-FUNCTION ANALYSIS, AND MICRO STIRRING CHIP (75) Inventors: Se Hyun Shin, Seoul (KR); Jeong Hun Nam, Seoul (KR); Hyun Jung Lim, Gyeonggi-do (KR)

(73) Assignee: Korea University Research and Business Foundation, Seoul (KR)

( * ) Notice: Subject to any disclaimer, the term of this patent is extended or adjusted under 35 U.S.C. 154(b) by 20 days.

(21) Appl. No.: 13/600,519

(22) Filed: Aug. 31, 2012

(65) Prior Publication Data
US 2014/0065715 A1  Mar. 6, 2014

(51) Int. Cl.
G01N 33/86 (2006.01)
G01N 33/48 (2006.01)
G01N 27/00 (2006.01)
G01N 21/07 (2006.01)

(52) U.S. Cl.
USPC ............ 436/69; 436/63; 436/150; 436/164; 436/165; 422/73; 422/82.01; 422/82.05; 422/82.09; 422/554; 435/13

(58) Field of Classification Search
USPC ............ 436/63, 69, 149, 150, 164, 165, 174, 436/177; 422/68.1, 73, 82.01, 82.02, 82.05, 422/82.09, 82.12, 533, 548, 554; 435/2, 13, 435/29
See application file for complete search history.

(56) References Cited

U.S. PATENT DOCUMENTS

| | | | | | |
|---|---|---|---|---|---|
| 4,066,360 | A | * | 1/1978 | Breddin et al. | 356/39 |
| 4,123,701 | A | * | 10/1978 | Josefsen et al. | 324/448 |
| 4,319,194 | A | * | 3/1982 | Cardinal et al. | 324/449 |
| 4,591,793 | A | * | 5/1986 | Freilich | 324/446 |
| 4,883,763 | A | * | 11/1989 | Holen et al. | 436/45 |
| 5,491,408 | A | * | 2/1996 | Rousseau | 324/71.1 |
| 6,004,818 | A | * | 12/1999 | Freilich et al. | 436/69 |
| 2007/0140902 | A1 | * | 6/2007 | Calatzis et al. | 422/58 |
| 2013/0094998 | A1 | * | 4/2013 | Roth et al. | 422/73 |

FOREIGN PATENT DOCUMENTS

| | | | |
|---|---|---|---|
| KR | 1020030014219 A | | 2/2003 |
| KR | 1020070001856 A | | 1/2007 |
| WO | 2008/072870 | * | 6/2008 |

OTHER PUBLICATIONS

Warwick S. Nesbitt, et al; "A shear gradient-dependent platelet aggregation mechanism drives thrombus formation", Nature Medicine, vol. 15, No. 6, pp. 665-675, published online May 24, 2009.
Yasuo Ikeda, et al; "The Role of von Willebrand Factor and Fibrinogen in Platelet Aggregation under Varying Shear Stress", J. Clin. Invest. vol. 87, Apr. 1991, pp. 1234-1240.

* cited by examiner

*Primary Examiner* — Maureen Wallenhorst
(74) *Attorney, Agent, or Firm* — Ladas & Parry LLP (57) ABSTRACT

An apparatus and method for platelet multi-function analysis using measurement of electrical characteristics, and a stirring microchip are provided. The apparatus for platelet multi-function analysis includes a stirring microchip that has a sample storage chamber formed therein to hold a blood sample, and in which an inner part of the sample storage chamber is coated with reagents composed of collagen and epinephrine, or collagen and ADP. The apparatus for platelet multi-function analysis further includes a microstirrer installed inside the stirring microchip to stir the blood sample and the reagents in the stirring microchip and a stirring induction unit configured to facilitate stirring of the microstirrer. Therefore, the platelet aggregation and multi-function analysis can be performed using a trace of blood, and the platelet aggregation and multi-function analysis can also be performed using the whole blood taken from the veins through a vacuum tube containing an anticoagulant.

18 Claims, 6 Drawing Sheets

APPARATUS AND METHOD OF PLATELET MULTI-FUNCTION ANALYSIS, AND MICRO STIRRING CHIP

BACKGROUND

1. Field of the Invention

The present invention relates to an apparatus and method for platelet multi-function analysis, and, more particularly, to an apparatus and method capable of measuring adhesion and aggregation of platelets within a short period of time using a trace of a blood sample, and a stirring microchip provided in the apparatus.

2. Discussion of Related Art

Thrombosis is a disease in which hemostasis or thrombus develops in blood vessels. When these symptoms appear in the coronary arteries of the heart or the brain blood vessels, heart attack or cerebral infarction is caused. Thus, this is called a "silent killer," and it has emerged as a major cause of death among modern people. This is problematic because such thrombosis or hemorrhagic symptoms are not diagnosed as genetic defects and have not been clearly identified yet.

Also, the more severe problem is that the morbidity of thrombosis tends to increase rapidly due to genetic and acquired factors. Therefore, there has been a demand for apparatuses and methods capable of quantitatively checking up thrombosis or hemorrhagic symptoms and making early diagnosis and prognosis based on the quantitative checkup.

Various factors associated with the hemostasis mechanism are present in damaged blood vessels. In this case, these factors have important biochemical and biophysical mechanisms. Among these, it has been known that platelets play a critical role in the hemostasis mechanism. Platelets does not have adhesion to intact blood vessel walls, but function to stop bleeding at a damaged blood vessel wall regardless of any flow conditions through action of both biochemical and biophysical mechanisms.

When the endothelium of blood vessels is damaged, ingredients such as collagen which constitute a material in the endothelium of blood vessels are exposed to the blood stream, and platelets are attached to these ingredients to be activated. The adhesion mechanism of the platelets has different characteristics depending on environments for the blood stream.

Specifically speaking, when a blood flow velocity is high as in arteries and a shear stress applied to the blood vessel walls is high, the platelets are not easily attached to the inner walls of blood vessels. However, since the platelets are activated under the conditions of a high shear flow field, they are easily attached to the blood vessel walls by means of a von Willebrand factor (vWF) that functions to facilitate adhesion to the blood vessel walls. Of course, it has been known that a glycoproteic receptor complex, GPIb-IX-V, which is present in cell membranes of the platelets, facilitates interaction with the vWF so as to attach the vWF to the cell membranes of the platelets.

Such attached platelets attract the same kinds of platelets to facilitate aggregation, thereby resulting in hemostasis, and then reinforcing a hemostatic action due to the presence of fibrin.

However, such functions of the platelets do not always work well, and may work adversely under certain flow conditions or situations. For example, when a blood vessel wall is locally stenosed due to arteriosclerosis, a part of the blood vessel wall through which platelets pass is exposed to a high shear rate so that the platelets can be activated, and adhesion/aggregation of the platelets takes place at the rear part of the stenosed blood vessel wall, thereby inducing thrombosis in which blood vessels are clogged (Nesbitt et al., A shear gradient-dependent platelet aggregation mechanism drives thrombus formation, Nature Medicine, 15:665-675, 2009).

As described above, the platelets and vWF are activated according to the size of blood flow, that is, the shear stress caused by the blood flow, and a hemostasis mechanism is realized due to an increase in adhesivity. It has been known that the shear stress required to activate the platelets or the vWF as described above is equal to and more than 8 Pa, and a shear rate is equal to and more than 5,000 1/s (Ikeda et al., The role of von Willebrand factor and fibrinogen in platelet aggregation under varying shear stress, J. Clinical Investigation, 87; 1234-1240, 1991).

To perform early diagnosis and prognosis of the hemostasis or thrombus symptoms as described above, various apparatuses have been proposed and developed. However, when the various apparatuses are classified using a measurement sensor, there are an electrical measurement system, an optical measurement system, and a system for measuring a hemostasis time.

Various methods and apparatuses have been developed together to subdivide and examine such functions of the platelets. The analysis of platelet functions is very important in discriminating a hemorrhagic disease caused by congenital or acquired platelet dysfunctions from a hemorrhagic disease in which there is no numerical abnormality in platelets. Also, this analysis of platelet functions tends to be increasingly used to determine an increase in hemorrhagic tendency due to an anti-platelet agent used to treat and prevent cardiovascular diseases or test resistance to drugs.

In general, the analysis of platelet functions is often performed to check congenital platelet dysfunctions or used as a preoperative screening test. Particularly, a bleeding time (BT) test system has been used for important analysis to discriminate a hemorrhagic disease caused by congenital or acquired platelet dysfunctions from a hemorrhagic disease in which there is no numerical abnormality in platelets.

The BT test is a test for measuring a bleeding time that was developed approximately 100 years ago and has been used to screen platelet functions. However, the analysis of platelet functions used so far is difficult to standardize and clinical applicability is low, and thus an invasive method should be used. Thus, there is a demand for an objective method capable of measuring the platelet functions.

In recent years, a platelet function analyzer (for example, PFA-100) used for measuring the functions of the platelets is characterized in that the platelets aggregate by a vWF which is activated at a high shear rate. To measure the functions of the platelets, the whole blood is allowed to flow at a high shear rate through long capillary vessels. Then, a method of measuring gradual clogging of an orifice coated with ADP or epinephrine along with collagen as the platelet aggregate around the orifice using a pressure or flow rate has been performed.

To analyze such functions of the platelets, a test that should absolutely depend on functions of the vWF and is dependent on hematocrit (Hct) should be performed, but an anti-aspirin or anti-clopidogrel test should not be performed. Also, a two-step test is required to analyze the functions of the platelets, which results in an increase in test costs. Also, at least 360 µl of blood is required to analyze such functions of the platelets, a pressure should be measured to maintain a constant flow of blood at a high shear rate, and a syringe pump should also be continuously driven to correct the pressure when the pressure drops. The flow rate slows down as the orifice is gradually clogged. In this case, since the flow rate exponentially slows down, it is difficult to measure an exact closure time according to platelet aggregation, which makes it difficult to expect the closure time using a mathematical technique.

In particular, the blood sample should be exposed to a high shear rate for at least a predetermined time so as to activate the vWF. To do this, a method of flowing blood through a fairly long capillary vessel at a high velocity may be used in PFA-100. However, this method has problems in that it requires a great quantity of blood, and the vWF around the capillary wall having the maximum shear rate may be easily activated but the vWF disposed at a central region of the capillary wall having the minimum shear rate is not activated. As a result, the reproducibility of the test results may be low.

IMPACT from Diamed uses a cone plate-type rotational Couette flow system to apply a constant shear stress to blood filled therein. Therefore, this is a method of measuring an adhesion level of platelets when a high shear stress is applied to the blood. This has a problem in that, like PFA-100, it is highly dependent on concentrations and functions of vWF and fibrinogen.

Verify-NOW (Accumetrics) uses a principle of measuring turbidity as an aggregation level of platelets using an optical sensor. This is a method in which an agonist is mixed with blood and reacted with microbeads whose surfaces are coated with collagen to induce aggregation of platelets in blood, and the aggregation of platelets is measured as turbidity with time. Thus, this method is often used even though it has the same technical problems as a variety of conventional methods of measuring turbidity.

SUMMARY OF THE INVENTION

The present invention is directed to providing an apparatus and method for platelet multi-function analysis capable of performing multi-function analysis of platelets by adjusting a rotational velocity of a microstirrer to generate blood flow at a proper shear rate in a stirring microchip since a microchip is simply and easily provided without requiring technical knowledge on operation and analysis for measuring a platelet multi-function and a microstirrer is provided in the stirring microchip, and thus analyzing a small amount of a blood sample taken from a vein or a fingertip using the stirring microchip, and a stirring microchip provided in the apparatus for platelet multi-function analysis.

The present invention is not limited to the technical objects according to the present invention, and it should be understood that the other objects which are not described in this specification are apparent from the detailed description of the invention to those skilled in the art to which the present invention belongs.

One aspect of the present invention provides an apparatus for platelet multi-function analysis including a stirring microchip having a sample storage chamber formed therein to hold a blood sample, and containing a reagent for platelet aggregation, a microstirrer installed inside the stirring microchip to induce the shear flow in the blood sample, a stirring induction unit configured to induce stirring of the microstirrer, a sensor installed inside the stirring microchip to measure adhesion and aggregation levels of platelets, and a control unit configured to control operation of the stirring induction unit and process a signal measured by the sensor.

An inner surface of the sample storage chamber may be coated with the reagent.

The reagent may be supplied to the blood sample by injecting the reagent in a liquid phase into the microstirrer, sealing the microstirrer, and then removing a sealed portion by means of a centrifugal force.

The sensor may be one of an electrode sensor configured to measure electrical impedance, and an optical sensor configured to measure turbidity.

The reagent may include a reagent selected from the group consisting of a mixture of fibrinogen and arachidonic acid (for measuring aspirin resistance), a mixture of collagen and epinephrine, a mixture of collagen and ADP, a mixture of collagen and arachidonic acid, a mixture of collagen and ADP-PGE1 (P2Y12 assay), a mixture of collagen and MRS2179, and a mixture of collagen and MRS2395, which may be used alone or in combination.

The stirring induction unit may include an actuator configured to provide power, a driving unit configured to receive the power from the actuator to be driven, and a magnetic body provided in an upper surface of the driving unit to drive the microstirrer arranged thereon using a magnetic force.

A rotational velocity and a rotation time of the microstirrer may be controlled under the control of the stirring induction unit, and a stopper hooked at one side of the driving unit to suddenly stop the stirring induction unit may be provided in the stirring induction unit.

The sensor may be composed of two electrodes in the sample storage chamber to calculate a change in adhesion and aggregation of the platelets in the sample storage chamber as an electrical signal.

The electrodes may be upper and lower electrodes installed respectively at upper and lower plates of the stirring microchip.

The upper and lower electrodes may be formed in a ring shape with a cut portion.

The upper and lower electrodes may have a plurality of electrodes radially disposed therein to have different diameters.

The upper and lower electrodes may be disposed outside the microstirrer.

The sensor may be composed of a light source and an optical measurement sensor, which are disposed at upper and lower portions of the sample storage chamber, respectively.

The stirring microchip may be used as a disposable microchip.

The apparatus for platelet multi-function analysis may further include an output unit configured to output the adhesion and aggregation levels of the platelets measured at the control unit and the measured results of the platelets.

The apparatus for platelet multi-function analysis may further include a chamber configured to hold the stirring microchip therein so as to maintain the thermal equilibrium.

The apparatus for platelet multi-function analysis may further include a temperature regulator configured to control a temperature so as to maintain a constant temperature of the blood sample.

Another aspect of the present invention provides a method for platelet multi-function analysis. Here, the method may include generating a high shear flow by injecting a blood sample into a stirring microchip and stirring the blood sample, measuring electrical characteristics of the blood sample according to an aggregation level of platelets using electrodes, and measuring an aggregation level and an aggregation characteristic time of the platelets using a change in the measured electrical characteristics with time.

In the measuring of the electrical characteristics using the electrodes, an aggregation level and an aggregation characteristic time of the platelets may be measured based on the fact that an electrical impedance value that is low at the beginning increases as the platelets that are a non-conductive material are attached and aggregated.

BRIEF DESCRIPTION OF THE DRAWINGS

The above and other objects, features and advantages of the present invention will become more apparent to those of ordinary skill in the art by describing in detail exemplary embodiments thereof with reference to the attached drawings, in which.

DETAILED DESCRIPTION OF EXEMPLARY EMBODIMENTS

With reference to the appended drawings, exemplary embodiments of the present invention will be described in detail below. To aid in understanding the present invention, like numbers refer to like elements throughout the description of the figures, and the description of the same elements will be not reiterated.

Figure 1:
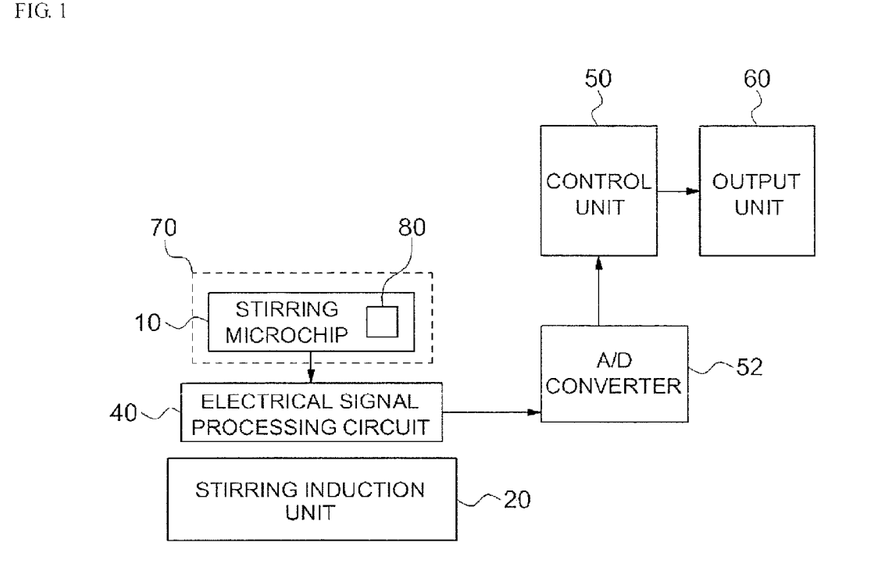
FIG. 1 is a block diagram showing an apparatus for platelet multi-function analysis according to one exemplary embodiment of the present invention.

FIG. 1 is a block diagram showing an apparatus for platelet multi-function analysis according to one exemplary embodiment of the present invention.

Referring to FIG. 1, the apparatus for platelet multi-function analysis according to one exemplary embodiment of the present invention generally includes a stirring microchip 10, a stirring induction unit 20, an electrical signal processing circuit 40 and a control unit 50.

Figure 2:
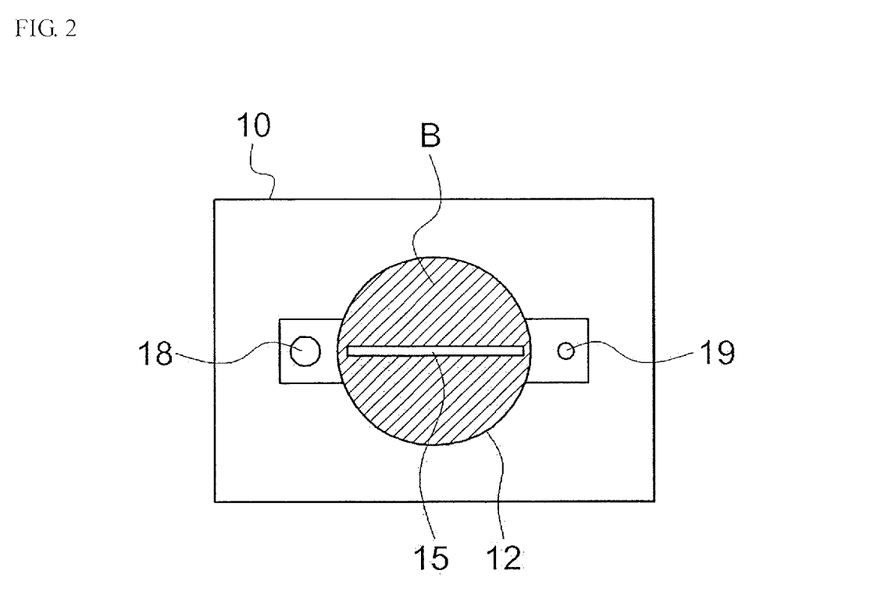
FIG. 2 is a plane view showing a disposable stirring microchip of the apparatus for platelet multi-function analysis according to one exemplary embodiment of the present invention.

First, a configuration of the stirring microchip 10 will be described with reference to FIGS. 2 and 3. FIG. 2 is a plane view showing a disposable stirring microchip of the apparatus for platelet multi-function analysis according to one exemplary embodiment of the present invention, and FIG. 3 is a lateral cross-sectional view showing a disposable stirring microchip and an electrode and stirring induction unit of the apparatus for platelet multi-function analysis according to one exemplary embodiment of the present invention.

Figure 3:
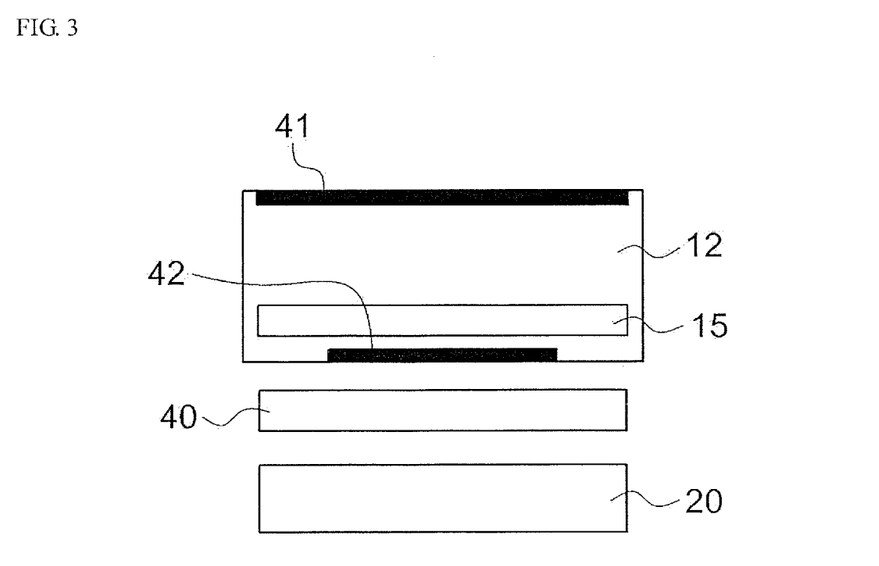
FIG. 3 is a side view showing a disposable stirring microchip, an electrode and a stirring induction unit of the apparatus for platelet multi-function analysis according to one exemplary embodiment of the present invention.

Referring to FIGS. 2 and 3, the stirring microchip 10 is a mini-kit for measuring a platelet multi-function, which is configured to hold a blood sample B therein. The stirring microchip 10 may be manufactured to be used as a disposable microchip. When the stirring microchip 10 is manufactured for disposable use as described above, a miniaturized mechanism may be used to easily measure an aggregation level of platelets from a trace of blood. The stirring microchip 10 may be formed of one material selected from a laser processable polymer, an injection-moldable polymer, and a ceramic material. Of course, the material of the stirring microchip 10 is not limited thereto.

Also, multiple chips in which a large number of the stirring microchips 10 are arranged may be provided to measure many blood samples at the same time or continuously measure the blood samples by loading the multiple chips onto equipment at once.

The stirring microchip 10 has a sample storage chamber 12 formed therein to directly hold blood. Also, an inlet 18 configured to input a blood sample B and an outlet 19 configured to discharge the air are formed at the stirring microchip 10. The sample storage chamber 12 is a space into which the blood sample B is directly injected, and which is manufactured in the form of an approximately circular chamber. The sample storage chamber 12 may be manufactured in various sizes according to a purpose of use. In general, the sample storage chamber 12 has a diameter of 1 to 10 mm and a depth of 0.1 to 5 mm. The disposable stirring microchip 10, including the sample storage chamber 12, may be manufactured to have optical transparency.

Next, a microstirrer 15 is installed inside the stirring microchip 10. The microstirrer 15 may be formed of a material that may be magnetized by an adjacent magnetic body, and the microstirrer 15 may be configured in one shape of a circular rod or circular tube having a linear or cruciform shape, and a circular plate having the central axis like a tack shape. The diameter or thickness of the microstirrer 15 may be approximately half the depth of the sample storage chamber 12, and the length or diameter of the microstirrer 15 may account to approximately 80% to 90% of the diameter of the sample storage chamber 12 in the stirring microchip 10.

The microstirrer 15 functions to mix a reagent provided in the sample storage chamber 12 with the injected blood sample B while stirring as the microstirrer 15 rotates at a proper rotational velocity. Also, when the microstirrer 15 rotates at a high rotational velocity, a high shear flow is induced. Then, such a high shear flow causes activation of platelets in blood to facilitate adhesion and aggregation of the platelets.

The microstirrer 15 may be formed of a thin metal material so that the microstirrer 15 can be magnetized by a magnetic force of a stirring induction unit 20 to be described below, and affected without mechanical connections. As shown in FIG. 2, the microstirrer 15 may also have a bar or rod shape, but may be manufactured in a bead shape. Since the microstirrer 15 is included in the stirring microchip 10, the microstirrer 15 may be disposable together with the stirring microchip 10 after use.

Also, since the microstirrer 15 is formed in a linear or cruciform cylindrical shape, the microstirrer 15 may be sealed to prevent a reagent to be tested from being exposed to the external air after the reagent is put into the microstirrer 15. Then, when the reagent put into the microstirrer 15 rotates at least a predetermined number of times, a sealed portion may be removed by a centrifugal force to cause release of the reagent.

The stirring induction unit 20 is a device which functions to activate the microstirrer 15 of the stirring microchip 10. Various kinds of the stirring induction unit 20 may be used as long as they can activate the microstirrer 15. For example, the stirring induction unit 20 is composed of an actuator (a motor), a driving unit (a round plate), and a magnetic body (a permanent magnet). Here, as the round plate is rotated by driving the motor while the permanent magnet is attached to a top surface of the round plate, rotation of the microstirrer 15 spaced a constant distance from the round plate is induced. Using an electromagnet, the stirring induction unit 20 may be configured without using a separate actuator such as a motor. As described above, the stirring induction unit 20 has advantages in that the platelets in blood may be activated by driving the microstirrer 15 through a magnetic drive mechanism to simply generate a high shear flow in the blood sample B and carry or discharge the input or coated reagent to a desired position.

In addition, the stirring induction unit 20 should be controlled to suddenly stop driving of the driving unit (a round plate). A stopper (not shown) configured to hook one side of the suddenly stopped driving unit is provided to stop the driving unit at an exact position. Stopping driving of the stirring induction unit 20 to suddenly stop the stirring is for the purpose of accurately measuring a platelet aggregation time.

Meanwhile, an electrical signal processing circuit 40 is positioned between the stirring microchip 10 and the stirring induction unit 20. Thus, the electrical signal processing circuit 40 functions to detect electrical signals measured through electrodes 41 and 42 and transfer the electrical signals to a control unit 50, as will be described below.

Figure 4:
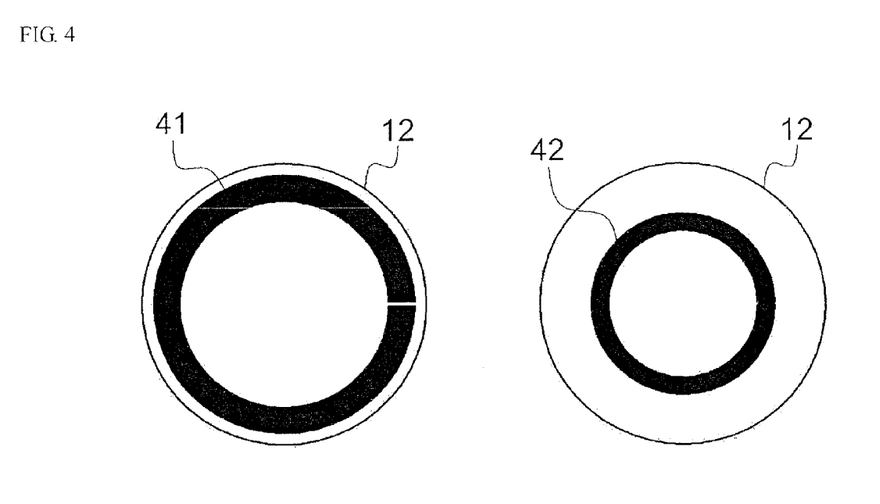
FIG. 4 is a plane view showing electrodes formed on top and bottom surfaces of the disposable stirring microchip according to one exemplary embodiment of the present invention.

The electrodes 41 and 42 may be provided in the stirring microchip 10 so that the electrical characteristics according to an aggregation level of platelets can be monitored with time. Specific configurations of the electrodes 41 and 42 are shown in FIG. 4. A basic configuration of each electrode is realized so that the upper electrode 41 and lower electrode 42, both of which have a ring shape, are disposed on upper and lower plates in the stirring microchip 10, respectively. In this exemplary embodiment, formation of the electrodes 41 and 42 in a ring shape is performed so as to minimize an effect on resistivity value between the electrodes 41 and 42 regardless of the position at which the microstirrer 15 provided to be able to rotate inside the stirring microchip 10 is stopped. Of course, the electrodes 41 and 42 may be formed in various shapes in addition to the ring shape shown in FIG. 4.

Surfaces of the electrodes 41 and 42 are coated with a suitable reagent so that a vWF activated by the stirring can be easily attached to the electrodes 41 and 42. A mixture of collagen and ADP, or a mixture of collagen and epinephrine is used as the reagent. The activated vWF is first attached onto a coated material, and acts as a place to which the platelets may be attached again. Thus, the platelets start to be attached and aggregated onto the electrodes 41 and 42 formed respectively on the upper and lower plates.

Here, an aggregation level of the platelets that are attached and aggregated by the activated vWF after stirring of the stirring induction unit 20 is measured at the electrical signal processing circuit 40. That is, an electrical resistivity is low before adhesion/aggregation of the platelets takes place between the upper electrode 41 and the lower electrode 42, but a change in electrical impedance value or capacitance value is caused when the platelets start to be attached and aggregated.

More particularly, referring to FIG. 4, the electrodes 41 and 42 are formed in a ring shape with a cut portion. As shown in FIG. 4, the upper electrode 41 and the lower electrode 42 may be disposed on the upper and lower plates in the stirring microchip 10 so that the upper electrode 41 and the lower electrode 42 can have different diameters, and may be disposed at facing positions to have the same diameter and thickness. Here, the electrodes 41 and 42 are not necessarily formed on the upper and lower plates, and may be formed at side plates.

Figure 5:
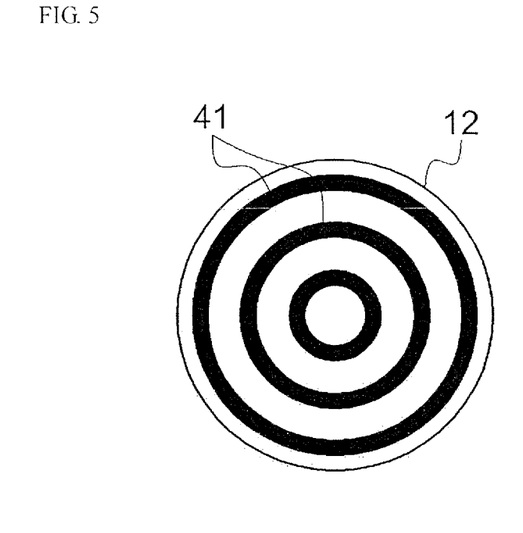
FIG. 5 is a plane view showing another exemplary embodiment of electrodes formed on the disposable stirring microchip according to one exemplary embodiment of the present invention.

Meanwhile, FIG. 5 is a plane view showing another exemplary embodiment of the electrodes formed on the disposable stirring microchip according to the present invention. Referring to FIG. 5, the upper electrode 41 may have a plurality of electrodes formed therein to have different diameters. Of course, the lower electrode 42 may also have a plurality of electrodes formed therein as shown in FIG. 5. In this case, it is possible to measure electrical resistivity between radially adjacent electrodes.

Figure 6:
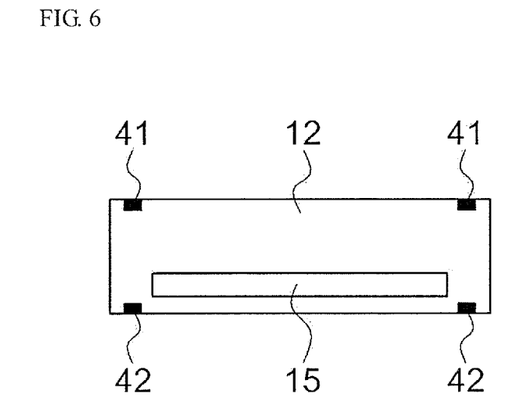
FIG. 6 is a side view showing still another exemplary embodiment of electrodes formed on the disposable stirring microchip according to one exemplary embodiment of the present invention.

FIG. 6 is a side view showing still another exemplary embodiment of the electrodes formed on the disposable stirring microchip according to the present invention. Referring to FIG. 6, the upper electrode 41 and lower electrode 42 may be disposed so that the upper electrode 41 and lower electrode 42 can be positioned outside the microstirrer 15 so as to minimize an effect of the microstirrer 15. That is, since the microstirrer 15 is not positioned between the upper electrode 41 and lower electrode 42 in this arrangement, the microstirrer 15 may minimize the effect on electrical resistivity between the electrodes 41 and 42.

Figure 7:
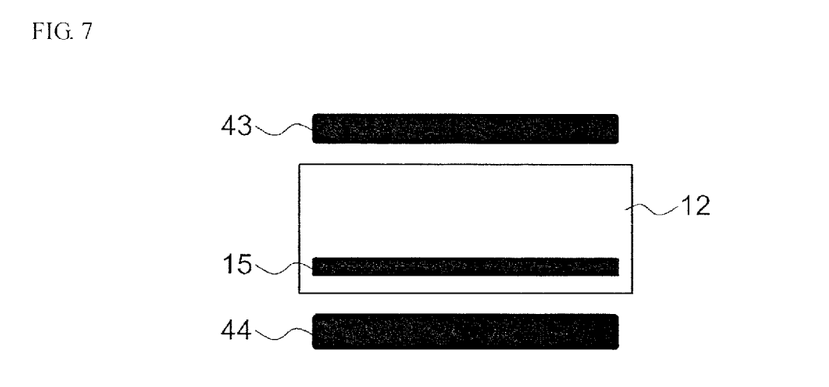
FIG. 7 is a side view showing a configuration of a sensor of the disposable stirring microchip according to one exemplary embodiment of the present invention.

FIG. 7 is a side view showing still another exemplary embodiment in which a light source 43 and an optical measurement sensor 44 are formed respectively on upper and lower portions of the sample storage chamber 12 as another configuration of a sensor. Referring to FIG. 7, an aggregation level of the platelets may be measured by measuring a change in light intensity at the optical measurement sensor 44 according to the aggregation level of the platelets when a capacity of light emitted from the light source 43 having a constant intensity passes through the sample storage chamber 12.

Figure 8:
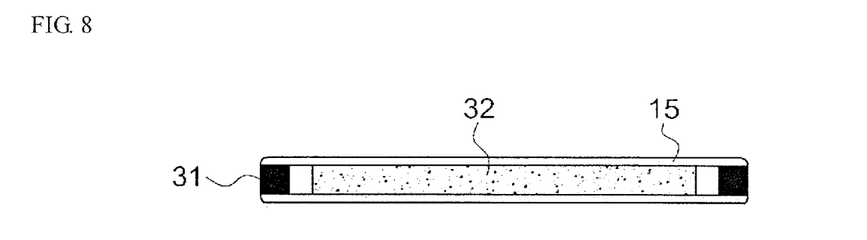
FIG. 8 is a side view showing that an inner part of a microstirrer of the disposable stirring microchip is filled with a reagent according to one exemplary embodiment of the present invention.

FIG. 8 is a cross-sectional view showing one exemplary embodiment in which an inner part of the microstirrer is filled with a reagent. Referring to FIG. 8, an inner part of the microstirrer 15 in a hollow and linear cylindrical shape is filled with a target reagent 32 to be tested in a liquid or solid state, isolated from the external air, and sealed by means of a membrane or sealing agent 31. When the microstirrer 15 containing the reagent rotates at a rate greater than a given rotational velocity, a sealed portion is removed by a centrifugal force to cause release of the reagent from the microstirrer. Then, the released reagent is mixed with blood B in the sample storage chamber 12. In this case, the mixing may be realized more rapidly through rotation of the microstirrer.

Meanwhile, the control unit 50 functions to process signals generated at the electrodes 41 and 42. Also, the control unit 50 functions to measure an electrical signal flowing in a blood sample B using the electrodes 41 and 42, receive the measured electrical signal through the electrical signal processing circuit 40 and record and store a change in electrical signal value with time. The control unit 50 controls an A/D converter 52 to convert an analog signal generated at the electrodes 41 and 42 into an analog signal. Also, the control unit 50 functions to control operation of the stirring induction unit 20.

The apparatus for platelet multi-function analysis according to the present invention further includes an output unit 60 configured to output adhesion and aggregation levels of the platelets measured at the control unit 50 and the measured results of the platelets. The output unit 60 may include a screen or printer configured to output an aggregation level of platelets measured at measuring sensors 43 and 44 and a change in electrical characteristics measured through the electrodes 41 and 42, and a storage unit configured to store data transmitted to/from the control unit 50.

Further, the apparatus for platelet multi-function analysis according to the present invention may further include a chamber 70 configured to have the stirring microchip 10 provided therein to maintain the thermal equilibrium, and a temperature regulator 80 configured to be able to maintain a constant temperature of the blood sample B and adjust a temperature of the blood sample B to an expected temperature and maintain the expected temperature of the blood sample B.

Meanwhile, a blood solution taken using sodium citrate as an anticoagulant may be used as the blood sample B that is used for measurement of this exemplary embodiment. Such blood treated with the anticoagulant does not coagulate since a calcium component present in plasma is removed by absorption. To measure a coagulation time, calcium ions are added to a blood sample containing the anticoagulant together with the reagent to artificially cause blood coagulation.

Hereinafter, the method for platelet multi-function analysis having the above-described configuration according to the present invention will be described in detail.

Figure 9:
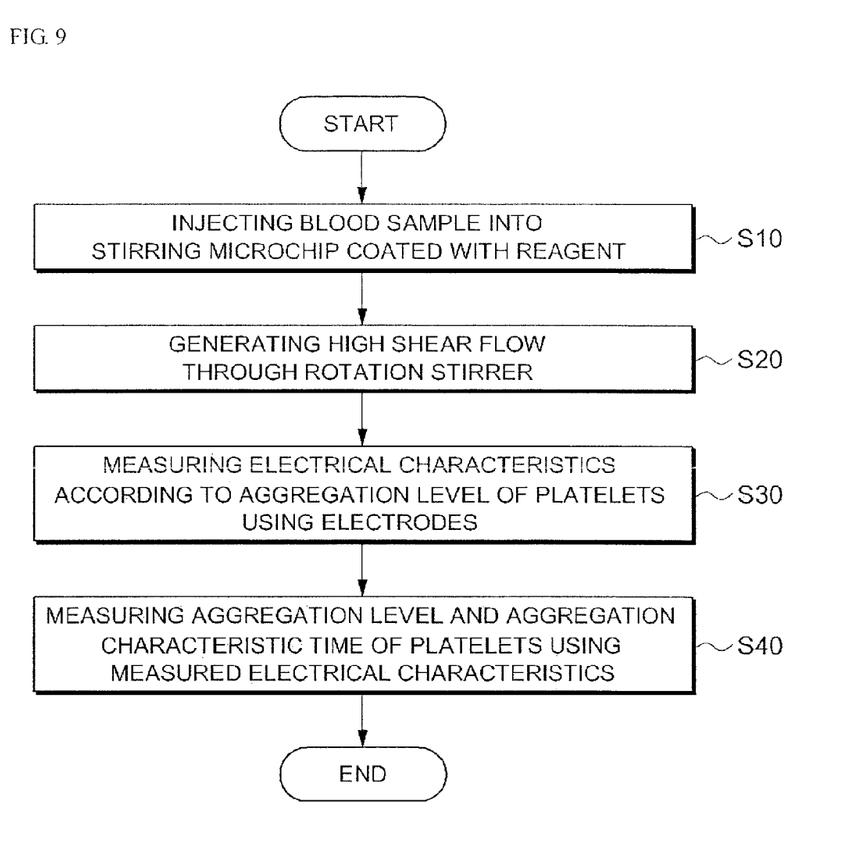
FIG. 9 is a flowchart illustrating a method for platelet multi-function analysis according to one exemplary embodiment of the present invention.

FIG. 9 is a flowchart illustrating a method for platelet multi-function analysis according to one exemplary embodiment of the present invention. Referring to FIG. 9, first, a blood sample B taken from a vein is injected into the sample storage chamber 12 of the stirring microchip 10 using a vacuum tube (i.e., Vacutainer) containing an anticoagulant (S10).

Next, the microstirrer 15 disposed in the disposable stirring microchip 10 is driven using a magnetic drive mechanism of the stirring induction unit 20 (S20). The stirring induction unit 20 is driven by means of a motor to rotate the driving unit, and the microstirrer 15 is rotated together by means of a magnetic body provided in the driving unit. In this case, the blood sample B may be stirred to apply a certain shear rate by rotating the blood sample B at a predetermined rotational velocity for a predetermined time. The vWF activated by the stirring of the blood sample B reacts with the reagent provided in the sample storage chamber so that the vWF can be attached onto the electrodes. Then, since the vWF attached onto the electrodes acts as a place to which the platelets may be attached again, the platelets start to be attached and aggregated onto the upper and lower electrodes 41 and 42.

When the reagent 32 sealed in the microstirrer 15 rotates at a rate greater than a given rotational velocity, a sealed portion is removed, and the reagent 32 is supplied into the sample storage chamber 12.

Subsequently, a change in electrical characteristics according to the adhesion and aggregation levels of the platelets attached to the upper and lower electrodes 41 and 42 is measured with time, and stored (S30). Here, an aggregation level and an aggregation characteristic time of the platelets are measured based on the fact that an electrical impedance value that is low at the beginning increases as the platelets are attached and aggregated.

An aggregation level and aggregation characteristic time of the platelets may be measured by calculating light transmission characteristics according to the elapse of time instead of the electrical characteristics.

Finally, the aggregation level and aggregation characteristic time of the platelets are measured using the measured values of the electrical characteristics (S40).

According to the present invention, since a stirring microchip is used, a trace of blood may be used to measure multi-functions of platelets. To generate the high shear rate that causes activation of the platelets, a conventional vacuum forming apparatus for allowing blood to flow through a long capillary vessel using a high difference in pressure is also required, but this may be replaced in the present invention by simply rotating the microstirrer.

Also, activation of the platelets may be precisely adjusted by controlling a shear rate under the control of the rotational velocity of the microstirrer, and an aggregation characteristic time of the platelets may be readily and simply measured by measuring the rotational velocity of the microstirrer as an electrical characteristic. Also, the entire system of a measuring apparatus is portable, and may be manufactured as a small-scale system which may be readily used at medical examination sites.

In addition, since disposable stirring microchips are formed at the entire portion in contact with a blood sample, a real-time clinical test may be highly effectively applied at medical examination sites.

Additionally, a multi-aid kit, which is composed of a number of stirring microchips, may be provided to measure a great quantity of samples at the same time or continuously measure the samples. Therefore, unlike conventional PFA-100, the multi-aid kit has an effect of mitigating inconvenience since a user need not manually exchange kits with each blood sample the user handles. Further, the blood flow in blood vessels may be substantially similarly measured as in stenosis according to the radii of the electrodes formed in the stirring microchip.

Also, when the reagent is provided outside the microstirrer by coating, the shelf life of the reagent may be problematic, but problems caused during a period of circulation may be solved when the reagent is stored in the microstirrer which is sealed, and when the stirring microchip configured thus is refrigerated.

In addition, since various reagents are supplied respectively to sample storage chambers as necessary, a drug response test on platelets may be effectively performed.

Furthermore, reagents supplied through rotation of the microstirrer may be effectively mixed into the blood sample within a short period of time, and a high shear flow field may be formed with an increase in rotational velocity, thereby achieving activation of the platelets.

While the invention has been shown and described with reference to certain exemplary embodiments thereof, it will be understood by those skilled in the art that various changes in form and details may be made therein without departing from the scope of the invention as defined by the appended claims.

What is claimed is:

1. An apparatus for platelet multi-function analysis comprising:
   a stirring microchip having a sample storage chamber formed therein to hold a blood sample, and containing a reagent for platelet aggregation;
   a microstirrer installed inside the stirring microchip to induce a shear flow in the blood sample;
   a stirring induction unit configured to induce stirring of the micro stirrer;

a sensor installed inside the stirring microchip to measure adhesion and aggregation levels of platelets; and a control unit configured to control operation of the stirring induction unit and process a signal measured by the sensor, wherein the reagent is supplied to the blood sample by injecting the reagent into the microstirrer, sealing the microstirrer by means of a membrane installed at both sides of the microstirrer, and removing the the membrane by means of a centrifugal force.

2. The apparatus of claim 1, wherein an inner surface of the sample storage chamber is coated with the reagent.

3. The apparatus of claim 1, wherein the sensor is one of an electrode sensor configured to measure electrical impedance, and an optical sensor configured to measure turbidity.

4. The apparatus of claim 1, wherein the reagent is selected from the group consisting of fibrinogen, arachidonic acid, collagen, epinephrine, adenosine diphosphate, adenosine diphosphate prostaglandin E1, 2'-deoxy-N6-methyl adenosine 3',5'-diphosphate, 2,2-dimethyl-propionic acid 3-(2-chloro-6-methylaminopurin-9-yl)-2-(2,2-dimethyl-propionyloxymethyl)-propyl ester, and a mixture thereof.

5. The apparatus of claim 1, wherein the stirring induction unit comprises:

an actuator configured to provide power;

a driving unit configured to receive the power from the actuator to be driven; and a magnetic body provided in an upper surface of the driving unit to drive the microstirrer arranged thereon using a magnetic force.

6. The apparatus of claim 5, wherein a rotational velocity and a rotation time of the micro stirrer is controlled under the control of the stirring induction unit, and a stopper hooked at one side of the driving unit to suddenly stop the stirring induction unit is provided in the stirring induction unit.

7. The apparatus of claim 1, wherein the sensor is composed of two electrodes in the sample storage chamber to calculate a change in adhesion and aggregation of the platelets in the sample storage chamber as an electrical signal.

8. The apparatus of claim 7, wherein the electrodes are upper and lower electrodes installed respectively at upper and lower plates of the stirring microchip.

9. The apparatus of claim 8, wherein the upper and lower electrodes are formed in a ring shape with a cut portion.

10. The apparatus of claim 8, wherein the upper and lower electrodes have a plurality of electrodes radially disposed therein to have different diameters.

11. The apparatus of claim 8, wherein the upper and lower electrodes are disposed outside the microstirrer.

12. The apparatus of claim 1, wherein the sensor is composed of a light source and an optical measurement sensor, which are disposed at upper and lower portions of the sample storage chamber, respectively.

13. The apparatus of claim 1, wherein the stirring microchip is usable as a disposable microchip.

14. The apparatus of claim 1, further comprising an output unit configured to output the adhesion and aggregation levels of the platelets measured at the control unit and the measured results of the platelets.

15. The apparatus of claim 1, further comprising a chamber configured to hold the stirring microchip therein so as to maintain thermal equilibrium.

16. The apparatus of claim 1, further comprising a temperature regulator configured to control a temperature so as to maintain a constant temperature of the blood sample.

17. A method for platelet multi-function analysis using the apparatus of claim 1, comprising:

generating a high shear flow by injecting a blood sample into a stirring microchip and stirring the blood sample;

measuring electrical characteristics of the blood sample according to an aggregation level of platelets using electrodes; and measuring an aggregation level and an aggregation characteristic time of the platelets using a change in the measured electrical characteristics with time.

18. The method of claim 17, wherein, in the measuring of the electrical characteristics using the electrodes, an aggregation level and an aggregation characteristic time of the platelets are measured based on the fact that an electrical impedance value that is low prior to the aggregation of the platelets increases as the platelets that are a nonconductive material are attached and aggregated to the electrodes.

* * * * *